United States Patent [19]

Hupperetz et al.

[11] Patent Number: 4,577,017

[45] Date of Patent: Mar. 18, 1986

[54] PROCESS FOR THE PREPARATION OF AN ISOCYANURATE COMPOUND CONTAINING ISOCYANATE GROUPS

[75] Inventors: Willem J. H. Hupperetz, Schinnen; Johannes A. H. M. Ramakers, Beek (L.), both of Netherlands

[73] Assignee: DSM Resins B.V., Zwolle, Netherlands

[21] Appl. No.: 649,609

[22] Filed: Sep. 12, 1984

[30] Foreign Application Priority Data

Sep. 13, 1983 [NL] Netherlands ............... 8303152

[51] Int. Cl.$^4$ ............................................ C07D 251/30
[52] U.S. Cl. .................................... 544/193; 544/222
[58] Field of Search ................................. 544/193, 222

[56] References Cited

U.S. PATENT DOCUMENTS

| | | | |
|---|---|---|---|
| 3,010,963 | 11/1981 | Erner | 252/182 |
| 3,652,424 | 3/1972 | Jackson et al. | 252/182 |
| 3,689,472 | 9/1972 | Emerson et al. | 544/193 |
| 3,716,535 | 2/1973 | Markiewitz | 544/193 |
| 3,730,919 | 5/1973 | McGinn | 260/2.5 |
| 3,892,687 | 7/1975 | Bechara et al. | 260/2.5 |
| 3,988,267 | 10/1976 | Bechara et al. | 252/426 |
| 4,302,351 | 11/1981 | Gras et al. | 252/182 |
| 4,359,550 | 11/1982 | Narayan et al. | 544/193 |
| 4,379,905 | 4/1983 | Stemmler et al. | 544/193 |
| 4,469,867 | 9/1984 | Disteldorf et al. | 544/222 |

FOREIGN PATENT DOCUMENTS

| | | | |
|---|---|---|---|
| 0024440 | 3/1981 | European Pat. Off. | 544/193 |
| 0056583 | 7/1982 | European Pat. Off. | 544/222 |

OTHER PUBLICATIONS

A. Davis, "The Catalytic of Ferric Acetyl Acetonate on the Rates of Dimerisation and Trimerisation of 2,4-Tolylene Diisocyanate", Makromol Chem. 77, pp. 185–190 (1964).

*Primary Examiner*—Henry R. Jiles
*Assistant Examiner*—J. G. Mullins
*Attorney, Agent, or Firm*—Cushman, Darby & Cushman

[57] ABSTRACT

Process for the preparation of an isocyanurate-compound containing isocyanate groups by trimerisation of a diisocyanate in the presence of
 a compound having the formula

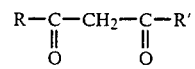

in combination with an organic base, or
a compound having the formula

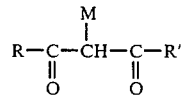

where R and R' are chosen from
 a hydrocarbon radical with 1–10 carbon atoms,
 —O—R$_1$, with R$_1$ being a hydrocarbon radical with 1–10 carbon atoms, and
 H.

10 Claims, No Drawings

PROCESS FOR THE PREPARATION OF AN ISOCYANURATE COMPOUND CONTAINING ISOCYANATE GROUPS

The invention relates to a process for the preparation of an isocyanurate compound containing isocyanate groups by trimerisation of a polyisocyanate in the presence of a catalyst.

BACKGROUND OF THE INVENTION

The European patent publication EP-A No. 56583 describes a process for trimerisation of a polyisocyanate, more in particular a diisocyanate, with the aid of a trimerisation catalyst, which, after the desired degree of conversion of the isocyanate has been reached, is deactivated by adding benzoyl chloride. Among the trimerisation catalysts mentioned are strong organic bases, tertiary-amine-cocatalyst combinations, Friedel-Crafts catalysts, basic salts of carboxylic acids, various alkalimetal compounds, onium compounds of nitrogen, phosphorus, arsenic, antimony, sulphur and selenium, and mono-substituted monocarbamic acid esters.

In the European patent publication EP-A No. 10589 several quaternary ammonium compounds are described as catalysts for the trimerisation of 1,6-hexanediisocyanate.

When trimers of polyisocyanates containing isocyanurate-rings obtained in this manner are applied in all kinds of coating-systems, the problem arises that the deactivating agent, for example benzoyl chloride, may also deactivate or at leat inhibit the catalyst systems commonly used for curing the coating. This is particularly true for catalyst systems on the basis of amines.

SUMMARY AND OBJECT OF THE INVENTION

The present invention provides a process for preparing an isocyanurate compound containing isocyanate groups by trimerizing a diisocyanate in the presence of a catalyst. The catalyst used is a compound having the formula:

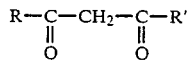

in combination with an organic base, or a compound having the formula:

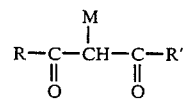

wherein the above formulas R and R' are independently selected from a 1-10 carbon atom hydrocarbon radical, $-O-R_1$ wherein $R_1$ is a 1-10 carbon atom hydrocarbon radical, and hydrogen and where in the second of the above formulas M represents a univalent metal.

One of the objects of the present invention is to provide a process for trimerisation of polyisocyanate yielding a product having little or no adverse effect on the catalyst system of the coating.

Another object is to provide a process with which isocyanurate compounds containing isocyanate groups can be prepared quickly and with a high yield.

DETAILED DESCRIPTION OF THE INVENTION

The invention relates to a process for the preparation of an isocyanurate compound containing isocyanate groups by trimerisation of a diisocyanate in the presence of a catalyst and is characterized in that the catalyst used is
I a compound having the formula

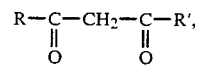

where R and R' have individually been chosen from the set of possibilities consisting of
a hydrocarbon radical with 1-10 carbon atoms,
$-O-R_1$, with $R_1$ being a hydrocarbon radical with 1-10 carbon atoms,
H, in combination with an organic base, or
II a compound having the formula:

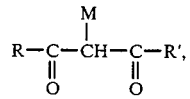

where R and R' have the same meanings as above, and M represents a univalent metal.

Suitable compounds are β diketones, such as, among others, pentadion-2,4, malonic esters, etc.

It is essential for the present process that besides the dicarbonyl compound an organic base is present. Examples thereof are alkalimetal alkanolates, for example sodium methanolate.

It is also possible to use an alkalimetal salt of the dicarbonyl compound. These compounds can be obtained in a simple manner by reacting the dicarbonyl compound with an alkalimetal salt, more in particular an alkalimetal alkanolate.

In this connection it is noted that from various publications it is known to use as trimerisation catalyst chelates of pentadione-2,4 with, for example, iron or cobalt. However, the present process is not based on the formation of a chelate. These publications contain no clue whatsoever to the fact that combination of such a β-dicarbonyl-compound and an organix base yields a very efficient catalyst for trimerisation of polyisocyanates.

The process can be conducted under the known trimerisation conditions.

In general, an amount of 0.001 to 25 mole % of β-dicarbonylcompound, relative to the polyisocyanate, is used. The ratio of the two catalyst components may vary within wide limits, for example from 30-70 mole % of β-dicarbonyl compound and from 70 to 30 mole % of base, relative to dicarbonyl compound plus base. However, the catalyst efficiency is optimum when the two components are present in approximately (mole-)equivalent amounts. The above-mentioned ratios relate to monofunctional catalyst components. If a dibasic base is used, the ratios obviously change according to the basicity of the base.

The temperature at which the reaction is carried out is preferably between −15° C. and 150° C., more in particular between 20° and 100° C., since at these temperatures relatively few side reactions occur. In particular at temperatures lower than −15° C. there is a chance that no isocyanurate compound is formed. The maximum temperature at which the reaction can be carried out is determined mainly by the fact that this type of catalyst becomes inactive at a high temperature.

The reaction can be carried out in the presence of a solvent or in pure polyisocyanate, depending on the reaction conditions to be chosen and the properties of the starting materials and reaction products.

As solvents for the reaction, those compounds are preferably used in which the polyisocyanates are soluble.

These are, among others, acetone, acetonitrile, acetophenone, allyl acetate, benzyl Cellosolve, bromobenzene, o-bromostyrene, o-bromotoluene, p-bromotoluene, butyl acetate, secbutyl acetate, butyl benzoate, butyl Cellosolve acetate, n-butylcyclohexane, carbon tetrachloride, Cellosolve acetate, 2-chloro-1,3-butadiene, chloroform, cyclohexane, cyclohexanone, dibutyl Cellosolve, dibutyl maleate, dibutylftalate, o-dichlorobenzene, m-dichlorobenzene, p-dichlorobenzene, 1,1-dichloroethane, dichloromethane, 1,1-diethoxybutane, 1,1-diethoxyethane, diethyl Cellosolve, diethyl maleate, diethyl ftalate, diethyl pimelate, diethyl succinate, diglycol diacetate, 1,3-dimethoxybutane, 1,1-dimethoxyethane, 3,3-dimethyl-2-butanone, 3,3-dimethylbutyl acetate, dimethyl Cellosolve, dimethyl ftalate, dimethyl pimelate, 2,5-dimethyltetrahydrofurane, 1,4-dioxane, phenyl ether, ethyl acetate, ethyl acrylate, ethyl butyrate, diethyl ether, ethyl formiate, 2-ethylhexyl acetate, ethyl propionate, m-ethyltoluene, o-ethyltoluene, p-ethyltoluene, glyceryl triacetate, glycol diacetate, glycol dipropionate, 2-heptanone, 3-heptanone, 4-heptanone, 3-hepten-2-one, 2-heptyl acetate, 3-heptyl-acetate, hexyl acetate, hexyl acrylate, hexylene glycol diacetate, hexyl hexanoate, methyl Cellosolve acetate, 5-methyl-2-hexanone, methyl propionate, 3-methylthiophene, 2-methylthiophene, 2-octanone, 3-pentanone, phenyl Cellosolve acetate, propyl acetate, propylene dichloride toluene, 1,1,2-trichloroethane, trichloroethylene, 1,2,3-trichloropropane, m-xylene, o-xylene, p-xylene, dimethyl formamide, dimethyl acetamide, dimethyl sulphoxide, N-methyl pyrrolidone, tetramethylene sulfone.

It is also possible to carry out the reaction in solvents in which the polyisocyanate is soluble but the reaction product is not soluble, so that the latter precipitates. Examples are decane, 2,2-dimethylbutane, 2,3-dimethylbutane, 2,4-dimethylbutane, 2,3-dimethylhexane, 3,3-dimethylhexane, 3,4-dimethylhexane, 2,5-dimethylhexane, 2,2-dimethylpentane, 2,3-dimethylpentane, 2,4-dimethylpentane, 3,3-dimethylpentane, 2,2-dimethylpropane, ethylcyclohexane, ethylcyclopentane, 3-ethylhexane, heptane, 1-heptene, 3-heptene-2-one, 2-methylheptane, 3-methylheptane, 4-methylheptane, 2-methylhexane, 3-methylhexane, 2-methylpentane, 3-methylpentane, 4-methyl-2-pentene, octane, 1-octene, and pentane.

The process is usually carried out under atmospheric pressure but, it is also possible, to carry out the process under increased or decreased pressure, depending on the nature of the compounds present in the reaction mixture.

After the desired conversion to trimer has been achieved, the catalyst system is deactivated by addition of a compound reacting acidically, for example a mineral acid or an acid chloride. Examples of suitable compounds are hydrochloric acid, phosphoric acid, sulphuric acid, acetic acid, trichloroacetic acid, oxalic acid, acetyl chloride, benzoyl chloride and the like. This acidically reacting compound is added in an amount equivalent to the amount of organic base. This constitutes a clear advantage of the present invention, since with state-of-the-art processes an excess of deactivator is desired. It is also possible to deactivate the catalyst by heating the reaction mixture to a temperature of about 100° C. to 150° C., depending on the catalyst type.

The present invention can be used for the preparation of isocyanurate compounds containing isocyanate groups starting from various types of polyisocyanates. As already indicated, the invention is more particularly aimed at diisocyanates, such as 1,5- and 1,6-hexanediisocyanate and isophoronediisocyanate. The process according to the invention can also be carried out with a mixture of polyisocyanates (a number of polyisocyanates that can be applied are listed in EP-A No. 56583) and more particularly to diisocyanates, such as, for example a mixture of an aromatic and an aliphatic diisocyanate. In addition, the process can be used with aromatic diisocyanates.

Preferentially, the process according to the invention is used with 1,5-hexanediisocyanate, since with this diisocyanate a stable oligomer can be obtained in a simple manner and without too many side reactions occurring, which oligomer can be used in paints and lacquers with advantage.

The reaction is preferably carried out in such a manner that the amount of residual unbound polyisocyanate is not more than 2.0 wt %, in particular not more than 0.5 wt %. The concentration of NCO-groups in the oligomer is preferably between 10 and 25 wt %. The weight-average molecular weight preferably lies between 500 and 5000, more in particular between 500 and 1500.

The most suitable value of NCO-content and molecular weight may differ according to application. One skilled in the art can determine the most suitable value for each individual application in a simple way.

The invention also relates to the application of the isocyanurate compound containing isocyanate groups for the preparation of polyurethane resins, in particular the higher-quality applications of aliphatic diisocyanates, such as industrial wood lacquers, motor car (repair) lacquers, aeroplane lacquers, leather finishes, textile coatings, tube or pipe coatings and the like.

The invention will now be explained with the following examples.

EXAMPLES

At room temperature 0.4 g of pentadione-2,4 and 0.4 g of sodium methanolate were added to 2 cc of butyl acetate. Next, 2 cc 1,5-hexanediisocyanate was added to this mixture.

Immediately after addition of the isocyanate, the temperature rose to about 90° C., which caused catalyst deactivation. The degree of conversion to isocyanurate compound was 40%.

In a similar manner a subsequent test was carried out in which catalyst deactivation wae prevented by cooling the reaction mixture. In this way, a degree of conversion of 99% was achieved.

We claim:

1. Process for the preparation of an isocyanurate compound containing isocyanate groups by trimerizing a diisocyanate in the presence of a catayst, wherein the catalyst is:

I a compound having the formula

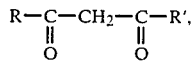

where R and R' are independently selected from the group consisting of:
a hydrocarbon radical with 1–10 carbon atoms,
—O—R₁ with R₁ being a hydrocarbon radical with 1–10 carbon atoms, and
H,
in combination with an alkalimetal alkanolate, or
II a compound having the formula

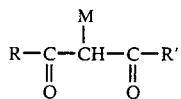

where R and R' have the same meanings as above, and M represents a univalent metal.

2. Process according to claim 1, wherein the pentadione-1,2 or its metal salt is used.

3. Process according to claim 1, wherein the alkalimetal alkanolate is sodium methanolate.

4. Process according to claim 1, wherein the reaction is carried out at a temperature of between 20° C. and 100° C.

5. Process according to claim 1, wherein the reaction is carried out in the presence of a solvent.

6. Process according to claim 1, wherein the catalyst is deactivated by heating.

7. Process according to claim 1, wherein the catalyst is deactivated by adding a compound reacting acidically with said catalyst.

8. Process according to claim 5, wherein the solvent is selected from the group consisting of: acetone, acetonitrile, acetophenone, allyl acetate, benzyl Cellosolve, bromobenzene, o-bromostyrene, o-bromotolulene, p-bromotoluene, butyl acetate, secbutyl acetate, butyl benzoate, butyl Cellosolve acetate, n-butylcyclohexane, carbon tetrachloride, Cellosolve acetate, 2-choloro-1,3-butadiene, chloroform, cyclohexane, cyclohexanone, dibutyl Cellosolve, dibutyl maleate, dibutylphthalate, o-dichlorobenzene, m-dichlorobenzene, p-dichlorobenzene, 1,1-dicholoroethane, dicholoromethane, 1,1-diethoxybutane, 1,1-diethoxyethane, diethyl Cellosolve, diethyl maleate, diethyl phthalate, diethyl pimelate, diethyl succinate, diglycol diacetate, 1,3-dimethoxybutane, 1,1-dimethoxyethane, 3,3-dimethyl-2-butanone, 3,3-dimethylbutyl acetate, dimethyl Cellosolve, dimethyl phthalate, dimethyl pimelate, 2,5-dimethyltetrahydrofurane, 1,4-dioxane, phenyl ether, ethyl acetate, ethyl acrylate, ethyl butyrate, diethyl ether, ethyl formiate, 2-ethylhexyl acetate, ethyl propionate, m-ethyltoluene, o-ethyltoluene, p-ethyltoluene, glyceryl triacetate, glycol diacetate, glycol dipropionate, 2-heptanone, 3-heptanone, 4-heptanone, 3-hepten-2-one, 2-heptyl acetate, 3-heptyl-acetate, hexyl acetate, hexyl acrylate, hexylene glycol diacetate, hexyl propionate, 3-methylthiophene, 2-methylthiophene, 2-octanone, 3-pentanone, phenyl Cellosolve acetate, propyl acetate, propylene dichloride toluene, 1,2,3-trichloropropane, m-xylene, o-xylene, p-xylene, dimethyl formamide, dimethyl acetamide, diemthyl sulphoxide, N-methyl pyrrolidone, tetramethylene sulfone, decane, 2,2-dimethylbutane, 2,3-dimethylbutane, 2,4-dimethylbutane, 2,3-dimethylhexane, 3,3-dimethlhexane, 3,4-dimethylhexane, 2,5-dimethylhexane, 2,2-dimethylpentane, 2,3-dimethylpentane, 2,4-dimethylpentane, 3,3-dimethylpentane, 2,2-dimethylpropane, ethylcyclohexane, ethylcyclopentane, 3-ethylhexane, heptane, 1-heptene, 3-heptene-2-one, 2-methylheptane, 3-methylheptane, 4-methylheptane, 2-methylhexane, 3-methylhexane, 2-methylpentane, 3-methylpentane, 4-methyl-2-pentene, octane, 1-ocetene, pentane and mixtures thereof.

9. Process according to claim 1 wherein said process an amount of 0.001 to 25 mole % of the β-dicarbonyl compound, relative to said polyisocyanate, is used.

10. Process according to claim 7 and wherein said process is catalyzed by the catalyst combination I, said catalyst is deactivated by adding said acidically reacting compound in an amount equivalent to the amount of said alkalimetal alkanolate, and said acidically reacting compound is selected from the group consisting of hydrochloridic acid, phosphoric acid, sulfuric acid, acetic acid, trichloroacetic acid, oxalic acid, acetyl chloride, and benzoyl chloride.

* * * * *